United States Patent [19]

Bernstein et al.

[11] Patent Number: 5,753,497
[45] Date of Patent: May 19, 1998

[54] DIAGNOSTIC ASSAY PROVIDING BLOOD SEPARATION

[75] Inventors: David Bernstein, Eldersburg; Mary Ann Childs, Baltimore, both of Md.; William Trainor, Hillsboro Beach, Fla.

[73] Assignee: Universal Health Watch Inc, Columbia, Md.

[21] Appl. No.: 577,105

[22] Filed: Dec. 22, 1995

[51] Int. Cl.⁶ .................................................. C12M 1/00
[52] U.S. Cl. .................................. 435/287.1; 435/287.2; 435/7.1; 435/2; 435/4; 435/810; 435/970; 436/518; 436/541; 436/524; 436/527; 436/528; 436/530; 436/63; 436/169; 436/514; 422/56; 422/60; 422/101; 422/58; 430/810; 430/824
[58] Field of Search .............................. 436/518, 541, 436/524, 527, 528, 530, 63, 169, 514; 422/56, 60, 101, 58; 435/7.1, 2, 4, 810, 970, 287.1, 287.2; 430/810, 824

[56] References Cited

U.S. PATENT DOCUMENTS

| | | |
|---|---|---|
| 4,477,575 | 10/1984 | Vogel et al. ........................ 436/170 |
| 5,166,051 | 11/1992 | Killeen et al. ........................ 435/7.1 |
| 5,186,843 | 2/1993 | Baumgardner et al. . |
| 5,234,813 | 8/1993 | McGeehan et al. . |
| 5,308,580 | 5/1994 | Clark . |
| 5,314,803 | 5/1994 | Wilk et al. . |
| 5,416,000 | 5/1995 | Allen et al. . |
| 5,435,970 | 7/1995 | Mamenta et al. . |
| 5,468,846 | 11/1995 | Chandler . |
| 5,500,187 | 3/1996 | Doems et al. . |

Primary Examiner—Paula K. Hutzell
Assistant Examiner—Heather Bakalyar
Attorney, Agent, or Firm—Foley & Lardner

[57] ABSTRACT

This invention provides a device and method for preparing a plasma enriched sample for use in an immunoassay strip. All parts that contact blood or a blood fraction remain in a container and prevent contamination from used blood. In one embodiment a sampling device collects blood and enters the container. A plasma enriched sample fills a plasma receptor which in turn is transferred to an immunoassay strip. Plasma is washed out of the strip by an aqueous solution. In another embodiment the sampling device doubles as a plasma separator. The invention allows sensitive and safe immunoassays to be performed on whole blood samples outside of the normal clinical laboratory setting.

13 Claims, 1 Drawing Sheet

DIAGNOSTIC ASSAY PROVIDING BLOOD SEPARATION

FIELD OF THE INVENTION

The present invention relates to devices and methods for obtaining a plasma enriched sample from a whole blood sample, and delivering the plasma enriched sample to a test strip for conducting an immunoassay.

BACKGROUND OF THE INVENTION

Most clinical assays for analytes in blood begin with a blood plasma or serum separation step to prevent red blood cells from interfering with the test procedure. Red blood cells typically constitute about half of the volume of a blood sample. Unless the red blood cells are substantially removed, their presence can affect clinical assay results that are sensitive to color. Whole blood also can interfere chemically. For example, hemoglobin that is released from red blood cells can affect the performance of certain clinical assays by virtue of the iron heme group which can act as a catalyst in some chemical reactions.

The conventional manner of separating serum or plasma from red blood cells is by centrifugation. However, recent advances in clinical test methods has led to the development of rapid test devices that can be used by untrained individuals outside of a laboratory setting. Centrifugation is not practical for use in these procedures. Consequently, an effort has been made within this field to develop and improve on simple red blood cell separators that do not require expensive or labor intensive instrumentation.

Early attempts to remove red blood cell interferences within a test strip have focussed on simple assay devices that do not require a wash or separation step. An example of one such attempt is U.S. Pat. No. 4,477,575 which describes a blood filter made from glass fiber that can separate out red blood cells when whole blood is slowly trickled onto one side. This blood filter was incorporated into a clinical assay test by physically affixing it to a reagent pad that contained reagents to and which produced a color in the presence of cholesterol. The '575 patent teaching, however, did not suggest how the blood filter could be used in a sensitive sandwich-type immunoassay test strip.

The use of membranes to separate plasma from red blood cells has been known for many years. One attempt to improve on this old procedure is described in U.S. Pat. No. 5,166,051. This patent describes hardening red blood cells by treating them with a crenating agent. Unfortunately many crenating agents affect chemical reactions. Furthermore, the red blood cell separator described by this patent was not adapted or suggested for a rapid and sensitive sandwich-type immunoassay test strip.

A related problem in the development of simple assay methods and kits has been the need to create a consistent sized test specimen that can combine with one or more chemistry reagents to generate a detection signal in a single device. Along with this general problem is the specific problem of safely handling blood samples that are suspected of harboring the HIV virus, hepatitis virus or other highly infectious, blood borne agents. Typically, during processing of such a sample for clinical testing, one or more vessels become contaminated, along with wash solutions and other test components such as stirrers and centrifugation tubes. The clinical tester must be protected from contact with parts and solutions that have been exposed to a blood sample or extracted blood sample. Any improvement in this area would greatly benefit clinical chemistry in view of the danger inherent in such blood contact, particularly where HIV testing is concerned.

SUMMARY OF THE INVENTION

Accordingly, it is an object of the present invention to greatly decrease the exposure of clinical testers to blood or blood extractions during a clinical blood test.

Another object of the invention is to decrease or eliminate the possibility of contact with used clinical test devices and reagents by others.

Yet another object of the invention is to simplify sandwich-type immunoassay clinical test devices and methods for their use to allow their greater acceptance outside the clinical laboratory.

These and other objects are realized by the a device according to this invention comprising a container having an opening for receiving a blood sample, and a transparent portion. A test strip having a receiving area for receiving a plasma enriched sample is positioned within the container such that a visible signal produced on the test strip can be observed through the transparent portion of the container. A hydrophilic blood collector adapted to receive a sample of blood is coupled to the container by a movable support (or tang), such that the collector can be moved into position proximate the opening in the container to deliver the blood sample into the opening. A red blood cell filter is positioned proximate to the opening in the container, such that the blood sample delivered to the opening contacts and passes through the filter. A plasma receptacle positioned within the container is adapted to receive a plasma enriched sample that passes through the filter. The receptacle is capable of movement within the container so as to be positionable in proximity of the receiving area of the test strip. The receptacle has a porous area through which the plasma enriched sample passes onto the receiving area of the test strip. Thereafter, the immunoassay proceeds in the normal course.

In another embodiment of the invention, a red blood a red blood cell agglutinator or binding agent is employed in the blood cell collector. The filter then may or may not be included. As a result, red blood cells of sampled blood become bound up in the collector and a plasma enriched sample is transferred to the plasma receptacle.

The objects are also achieved by a method for obtaining a plasma enriched sample and transferring it to a test strip. The method basically comprises carrying out an assay using a device in accordance with this invention.

The device and method described present a simple and quick means for separating blood plasma from whole blood, without the need for centrifugation. Moreover, the method and device provided permit the direct and rapid collection of a whole blood sample from a blood source, (such as a finger-prick or bleeding wound) via direct absorption into a blood collector. The invention is particularly useful in emergency situations, where there is a need for immediate collection and of a sensitive immunoassay test of a blood sample.

The method and device overcome the prior art problem of contamination of the tester from blood or blood components during the testing process itself. That is, all test components are present inside a container such that after a test is complete, all parts that contacted the blood or an extraction of the blood remain sealed within the container.

DETAILED DESCRIPTION OF THE PREFERRED EMBODIMENTS

Figure 1:
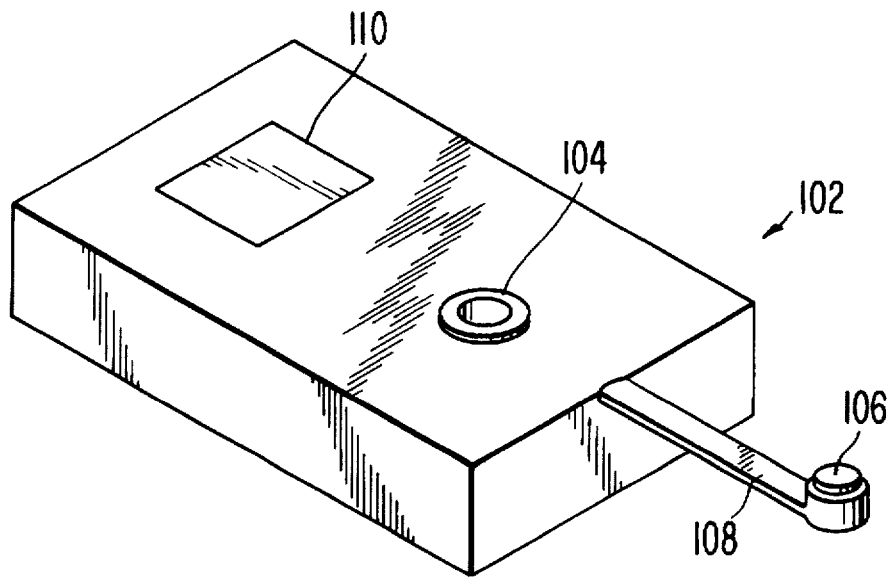
FIG. 1 depicts a device in accordance with this invention.

The present inventors surprisingly realized that a blood collector and a red blood cell filter could be integrated into a container for conducting a sensitive sandwich-type immunoassay, and done so in a manner that would enhance the safety of the person performing the assay. This revelation followed experimental work and theoretical innovation in ways to handle samples used in clinical immunoassays. Part of the discovery also stems from work performed with nitrocellulose membranes and means for applying blood plasma samples to these membranes.

Previous publications concerning blood separation techniques are directed to simple chemical tests and are generally not applicable to sandwich-type immunoassays. This is a natural consequence of the complexity of sandwich-type immunoassay methods in which a controlled plasma sample size is added at a controlled time to immunoassay reagents after separation of plasma from blood. The present invention overcomes these problems with a combination of mechanical and fluid elements inside a test container. The test container and all parts within are preferably disposable.

One aspect of a basic embodiment of the present invention is the controlled transfer of plasma into an immunoassay and subsequent timing of the immunoassay. This is achieved by a mechanical movement of a plasma receptacle. The mechanical movement can be carried out by any of a number of means to those skilled in the mechanical arts, especially regarding the engineering of plastic test devices.

A preferred embodiment is to move the plasma receptacle by pressing a blood collector or its support such that after transferring plasma enriched sample to the collector, additional pressure placed on the collector's movable support will displace the plasma receptacle from its position to a new position, e.g., directly below the prior position, where it contacts a receiving area of a test strip. In such an embodiment, the receptacle comprises a porous porting which permits transfer of the plasma to the strip. The strip also is within the same container as the plasma receptacle.

The present invention overcomes the prior art problem of sample contamination during and after a blood test by combining all test reagents and fluids within the test container. It is most preferred that the blood collector snap into the container opening during use so that no subsequent contamination is possible. In one embodiment an additional, sterilizing fluid is provided within the container so that the user can break a seal and flood possibly contaminated portions of the container with the sterilant.

The container may be comprised of any water insoluble material or combination of materials. Preferably, the container is made of plastic. The movable support which holds the hydrophilic blood collector advantageously is part of the container itself, and is flexible enough to allow the collector to contact a blood sample and then be moved into the opening of the container. More than one opening in the container is possible if the additional opening does not allow release of a blood component from the container during or after a test such as, for example, a vent hole. Preferably the container contains only a single opening which accepts the blood collector.

In one basic embodiment of the invention a red blood cell filter is positioned within the opening of the device such that upon entering the opening, the blood collector physically contacts the red blood cell filter and transfers blood or plasma enriched sample to it and cannot be removed from the opening.

The blood collector is comprised of a hydrophilic material that absorbs blood. Many such materials are known to skilled artisans and include porous plastic, paper, cellulose ester fiber mats, fiber glass and the like. The blood collector additionally may be comprised of an anticoagulant substance such as sodium EDTA, sodium citrate, heparin, and the like. The use of heparin is preferred.

In one embodiment of the invention, the blood collector both receives a blood sample and separates blood cells from plasma to release an enriched plasma fraction upon subsequent physical contact with another hydrophilic substance. In this embodiment, the blood collector is referred to as a collector-separator. The collector-separator can comprise one or more chemical substances to facilitate separation of red blood cells from blood plasma. A collector-separator generally may be used interchangeably with the collector in this invention, and any reference to a collector in this specification should be deemed also to be a reference to a collector-separator. Examples of chemical substances that can be suitable are thrombin, lectin, cationic polymers, antibodies against one or more red blood cell surface antigens and the like.

Polymers which have more than 10 positive charges per molecule and preferably more than 20 positive charges per molecule are suitable in principle. Especially preferred is Polybren®, in particular that which has a molecular weight of less than 6000.

Lectins include all that can bind human red blood cells but which are not blood-group specific. Potato lectins, tomato lectins and kermes berry lectins are preferred.

In one embodiment the chemical substance which facilitates separation of red blood cells from plasma within the collector-separator adheres to surfaces of the collector-separator, preferably by covalent means although, in the case for protein substances onto a collector-separator of glass or plastic composition, nonspecific absorption is preferred. In use, red blood cells become attached to the chemical substance(s) immobilized within the collector-separator and are substantially (less than 20 percent of red blood cells that enter the collector-separator matrix) not transferred along with enriched plasma to the plasma receptacle.

In another embodiment, the collector-separator comprises a red blood cell agglutinant which causes red blood cells to agglutinate. Many agglutinant are known to skilled artisans, including many of the above listed substances such as lectin and thrombin. In this embodiment the agglutinin is free and not itself immobilized within the collector-separator.

Generally, the collector-separator absorbent volume is at least twice the absorbent volume of the plasma receptacle, advantageously at least three times the volume of the plasma receptacle and most preferably at least five times the volume of the plasma receptacle. However, in one embodiment, a red blood cell filter is used and receives partly filtered blood from the collector-separator. In this case, the volume of blood collected by the collector-separator can be more than the absorbent volume of the collector-separator (blood adheres to the surface and does not all enter the container) and the volume of plasma enriched sample which passes through the red blood cell filter can be more than half the volume of the red blood cell filter. An advantage of this embodiment is that it can allow more rapid filtering of red blood cells.

The red blood cell filter is comprised of a hydrophilic material that allows blood plasma but not red blood cells to pass through. Many suitable materials are known to skilled artisans, and can include glass fibers, synthetic resin fibers, and membranes of various types. Especially preferred is Cytosep® (Gelman Sciences, Ann Arbor, Mich.) which is a composite of glass and natural fibers. The red blood filter can be in physical contact with a plasma receptacle such that upon wetting the filter with blood, a plasma enriched sample fraction enters the plasma receptacle.

In one embodiment the red blood cell filter is used in conjunction with a collector-separator to eliminate red blood cell interference from the immunoassay. In this embodiment, part of the red blood cells are removed by the collector-separator and part are removed by the filter. This optionally allows the collector-separator to become overfilled with blood (not all red blood cells enter the porous collector-separator), or to otherwise incompletely immobilize red blood cells. In this embodiment the red blood cell filter volume is preferably less than twice the volume of plasma enriched sample which passes through it.

The plasma receptacle is comprised of a hydrophilic material that receives the plasma enriched sample. It is preferably from 10 um to 3000 um thick and more preferably from 50 um to 500 um thick. Many suitable materials such as paper, nylon membrane, porous plastic and the like are known to skilled artisans. After wetting, the plasma receptacle can transfer enriched plasma to another hydrophilic material that it contacts. Advantageously, the plasma receptacle becomes filled with plasma and then is moved away from the blood collector to contact a test strip.

Optionally, the plasma receptacle can contain one or more agents that bind or immobilize red blood cells. These agents can comprise a chemical such thrombin, lectin, cationic polymers, antibodies against one or more red blood cell surface antigens and the like and they can comprise immobilized fibers such as fiber glass. By immobilizing, either chemically, or mechanically, or both, the plasma receptacle can further decrease interference by red blood cells to the immunoassay by preventing movement of red blood cells into the immunoassay strip. In this embodiment, the collector or collector-separator can contact the plasma receptacle directly without the need for a separate filter.

In yet a further embodiment, both the red blood filter and plasma receptacle are not used, but the above-mentioned red blood cell (chemical, mechanical or combination) immobilant is in or on the immunoassay test strip itself. In this embodiment the collector-separator contacts the immunoassay test strip directly. An added feature in this case is to place an absorbent below the contacted portion of the immunoassay test strip to encourage adsorption of fluid during the contact and increase the transfer of plasma enriched sample to the immunoassay test strip. In this case, control of the test strip thickness and/or underlying absorbent size can control the size of sample added to the immunoassay test strip.

The test strip contains one or more reagents for carrying out an immunoassay test, and such strips are well known to skilled artisans. The strip will include a receiving area which receives enriched plasma from plasma receptacle, or optionally from the filter or collector-separator.

The receiving area may be a portion of an immunochromatography strip such as a separation membrane. A preferred separation membrane is nitrocellulose. The receiving area may also be a water impermeable platform to which abut one or more separation materials that contains one or more test reagents of the immunoassay. In the latter case the enriched plasma material primarily exits the plasma receptacle from its edges and preferably the separation material which receives enriched plasma material is at least half the thickness of the enriched plasma material.

As used herein, the term plasma enriched sample means a sample of blood having a higher plasma concentration than the plasma concentration in an equal-volume sample of whole blood. Thus, the term plasma enriched sample can mean a sample whose plasma concentration is 10%, 20%, 30%, 40%, 50%, 60%, 70%, 80% 90% or greater than the concentration of plasma in the blood. Considered another way, a plasma enriched sample can be thought of in terms of the number of red blood cells removed from the whole blood sample. Thus, a plasma enriched sample is one in which 10%, 20%, 30%, 40%, 50%, 60%, 70%, 80% 90% or more of the red blood cells have been removed.

Referring now to the figures, a physical embodiment in accordance with the present invention is provided.

FIG. 1 depicts a device in accordance with this invention. A container 102 having opening 104 receives a blood sample from hydrophilic blood collector 106 held by movable support 108. Container 102 further comprises transparent portion 110 for viewing the results of the diagnostic assay.

Figure 2:
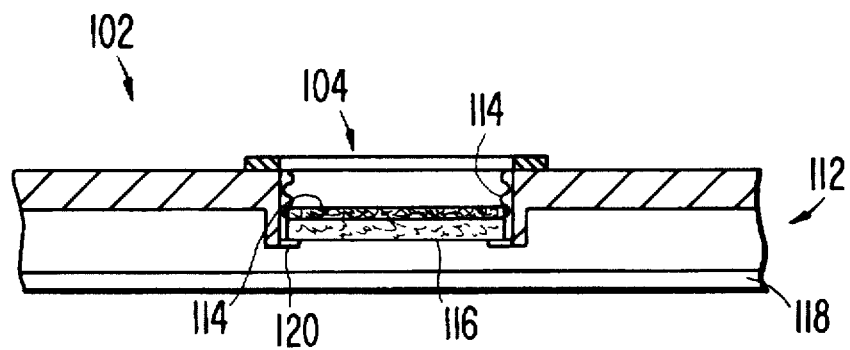
FIG. 2 depicts a cross section of the device in accordance with this invention.

FIG. 2 depicts a side view of opening 104 within wall 112 of the container. Red blood cell filter 114 is positioned along the wall and floor of opening 104. Opening 104 is large enough to admit blood collector 106. In this embodiment plasma receptacle 116 contacts the lower surface of red blood cell filter 114 and is positioned above test strip 118. Plasma receptacle 116 is held in place by plastic tabs 120.

During use, blood collector 106 is wetted by a blood sample. The user then bends movable support (or tang) 108 over so that collector 106 completely enters opening 104 and becomes locked in place. Collector 106 contacts red blood cell filter 114 and transfers blood to it. Enriched plasma is released from filter 114 and enters plasma receptacle 116. The user presses down harder on movable support 108 and thereby breaks and releases plastic tabs 120. The contact between plasma receptacle 116 and filter 114 is broken and plasma receptacle 116 is pushed down onto test strip 118.

In another embodiment collector 106 additionally functions to separate red blood cells from plasma and is termed collector-separator. In this embodiment red blood filter 114 is not required and collector-separator (106 in the figure) contacts plasma receptacle 116 directly.

It will be apparent to those skilled in the art that various modifications and variations can be made to the compositions and processes of this invention. Thus, it is intended that the present invention cover such modifications and variations, provided they come within the scope of the appended claims and their equivalents.

What is claimed is:

1. A device comprising:
   (a) a container for conducting an assay, the container having an opening for receiving a blood sample, and a transparent portion;
   (b) a test strip having a receiving area for receiving a plasma enriched sample, said test strip being positioned within said container such that a visible signal produced on said test strip can be observed through said transparent portion from outside of said container;
   (c) a hydrophilic blood collector for receiving a sample of blood, said collector being coupled to said container by a movable support, such that said collector can be moved into position proximate said opening in said container to close said container and deliver said blood sample into said opening;

(d) a red blood cell filter positioned proximate to said opening in said container, such that said blood sample delivered to said opening contacts said filter; and (e) a plasma receptacle positioned within said container, said plasma receptacle for receiving a plasma enriched sample that passes through said filter, said receptacle being capable of movement within said container so as to be in proximity of said receiving area, said receptacle having a porous area through which a quantity of said plasma enriched sample passes onto said receiving area.

2. The device of claim 1, wherein said blood collector is impregnated with an anticoagulant.

3. The device of claim 2, wherein said anticoagulant is sodium heparin.

4. The device of claim 1, wherein said red blood cell filter is a composite of glass and natural fibers.

5. The device of claim 1, wherein said red blood cell filter separates red blood cells by charge, size or chemical aggregation of said red blood cells.

6. A method for obtaining a plasma enriched sample and transferring it to a test strip, said method comprising the steps of:

(a) providing a blood sample to a hydrophilic blood collector, said collector being coupled to a container by a movable support, such that said collector can be moved into position proximate said opening in said container to deliver said blood sample into an opening in said container and seal said container;

(b) moving said collector into position proximate said opening in said container;

(c) transferring said blood through said opening to a red blood cell filter positioned within said container;

(d) permitting said blood sample to filter through said filter to provide an plasma enriched sample into a plasma receptacle positioned within said container; and (e) moving said plasma receptacle into contact with a test strip positioned within said container so as to permit transfer of a quantity of said plasma enriched sample onto said test strip.

7. The method of claim 6, wherein said red blood cells are filtered by charge, size, or aggregation of red blood cells by a chemical.

8. The method of claim 7, wherein said chemical is a lectin.

9. The method of claim 6, comprising the further step of:

(f) washing said plasma enriched sample from said receptacle and into said test strip by adding an aqueous solution to said receptacle.

10. The method of claim 6, wherein said strip test is an immunochromatographic strip test.

11. A device comprising:

(a) a container for conducting an assay, said container having an opening for receiving a blood sample, and a transparent portion;

(b) a test strip having a receiving area for receiving a plasma enriched sample, said test strip being positioned within said container such that a visible signal produced on said test strip can be observed through said transparent portion from outside of said container;

(c) a hydrophilic blood collector-separator adapted to receive a sample of blood, said collector-separator comprising a reagent that facilitates separation of plasma from red blood cells, said collector-separator being coupled to said container by a movable support, such that said collector-separator can be moved into position proximate said opening in said container to close said container and deliver a plasma enriched sample into said opening; and (d) a plasma receptacle positioned within said container, said plasma receptacle being adapted to receive a plasma enriched sample that passes through said opening, said receptacle being capable of movement within said container so as to be in proximity of said receiving area, said receptacle having a porous area through which a quantity of said plasma enriched sample passes onto said receiving area.

12. A device comprising:

(a) a container for conducting an assay, said container having an opening for receiving a blood sample, and a transparent portion;

(b) a test strip having a receiving area for receiving a plasma enriched sample, said test strip being positioned within said container such that a visible signal produced on said test strip can be observed through said transparent portion from outside of said container; and (c) a hydrophilic blood collector-separator adapted to receive a sample of blood, said collector-separator comprising a reagent that facilitates separation of plasma from red blood cells, said collector-separator being coupled to said container by a movable support, such that said collector-separator can be moved into position proximate said opening in said container to close said container and deliver a plasma enriched sample into said opening;

wherein said receiving area of said test strip is positioned proximate said opening such that a quantity of said plasma enriched sample is received on said receiving area.

13. A device comprising:

(a) a container for conducting an assay, said container having an opening for receiving a blood sample, and a transparent portion;

(b) a test strip having a receiving area for receiving a plasma enriched sample, said test strip being positioned within said container such that a visible signal produced on said test strip can be observed through said transparent portion from outside of said container;

(c) a hydrophilic blood collector for receiving a sample of blood, said collector being coupled to said container by a movable support, such that said collector can be moved into position proximate said opening in said container to close said container and deliver said blood sample into said opening; and (d) a red blood cell filter positioned proximate to said opening in said container, such that said blood sample delivered to said opening contacts said filter;

wherein said receiving area of said test strip is positioned proximate said opening such that said plasma enriched sample is received on said receiving area.

* * * * *